United States Patent [19]

Junino et al.

[11] Patent Number: 5,508,464
[45] Date of Patent: Apr. 16, 1996

[54] PROCESS FOR THE PREPARATION OF 5,6-DIHYDROXYINDOLE AND INTERMEDIATE COMPOUNDS

[75] Inventors: Alex Junino, Livry-Gargan; Jean J. Vandenbossche, Aulnay-sous-Bois; Gerard Lang, Saint-Gratien, all of France

[73] Assignee: L'Oreal, Paris, France

[21] Appl. No.: 480,297

[22] Filed: Jun. 7, 1995

Related U.S. Application Data

[62] Division of Ser. No. 339,236, Nov. 10, 1994, which is a continuation of Ser. No. 921,097, Jul. 29, 1992, Pat. No. 5,410,067, which is a continuation of Ser. No. 475,906, Feb. 5, 1990, abandoned, which is a continuation of Ser. No. 337,863, Apr. 14, 1989, abandoned, which is a continuation of Ser. No. 172,246, Mar. 23, 1988, abandoned, which is a continuation of Ser. No. 927,723, Nov. 7, 1986, abandoned.

[51] Int. Cl.⁶ .................................................. C07C 253/30
[52] U.S. Cl. ................................................................ 558/410
[58] Field of Search ................................................ 558/410

[56] References Cited

U.S. PATENT DOCUMENTS

| | | | |
|---|---|---|---|
| 3,976,695 | 8/1976 | Kaiser | 549/519 |
| 3,995,041 | 11/1976 | Havera | 546/95 |
| 4,088,763 | 5/1978 | Cyrus | 514/252 |
| 4,618,627 | 10/1986 | Murase | 514/699 |

OTHER PUBLICATIONS

Green, et al., "Protecting Groups in Organic Chemistry", (1981), pp. 90–91.
McOmie, "Protective Groups in Organic Chemistry", (1973), pp. 168–169.
Walker, J.A.C.S., 77, p. 3844 (1955).
Reitz, J. Med. Chem. 28, pp. 642–647 (1985).
Muralidar, Ind. J. Chem., 16B, p. 1004 (1978).
Translation of Japan 80/76859 (Fujimoto) (1980).
Translation of Japan 80/62061 (Ihara) (1980).

*Primary Examiner*—Joseph Paul Brust
*Attorney, Agent, or Firm*—Cushman Darby & Cushman

[57] ABSTRACT

Process for the preparation of 5,6-dihydroxyindole, wherein the compound of formula:

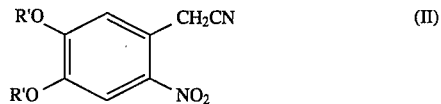

in which R' denotes a hydrogen atom or an optionally substituted benzyl radical, is subjected either to the action of hydrogen under pressure or to a hydrogen transfer operation, in a solvent medium and in the presence of a hydrogenation catalyst.

3 Claims, No Drawings

PROCESS FOR THE PREPARATION OF 5,6-DIHYDROXYINDOLE AND INTERMEDIATE COMPOUNDS

This is a division of application Ser. No. 08/339,236, filed Nov. 10, 1994 which is a continuation of application Ser. No. 07/921,097, filed Jul. 29, 1992, now U.S. Pat. No. 5,410,067, which is a continuation of application Ser. No. 07/475,906, filed Feb. 5, 1990, now abandoned, which is a continuation of application Ser. No. 07/337,863, filed Apr. 14, 1989, now abandoned, which is a continuation of application Ser. No. 07/172,246, filed Mar. 23, 1988, now abandoned, which is a continuation of application Ser. No. 06/927,723, filed Nov. 7, 1986, now abandoned.

The present invention relates to a new process for the preparation of 5,6-dihydroxyindole.

5,6-Dihydroxyindole is well known in the state of the art as playing a dominant part in the production of melanin. It would appear to be involved in the process of the formation of eumelanins from 3,4-dihydroxyphenylaniline [J. Biol. Chem. 172,83 (1948); Nature 276, 627 (1978)].

5,6-Dihydroxyindole has been described and used in dye compositions for dyeing keratinous fibres, and especially human hair. In particular, this forms the subject of French patents 1,133,594, 1,264,707, 2,390,158 of the applicants and 2,536,993.

Known preparative processes do not enable this compound to be prepared in a satisfactory manner, at least on an industrial scale, from inexpensive starting materials.

The processes for the preparations of 5,6-dihydroxyindole which are generally referred to make use of 2,β-dinitrostyrene, disubstituted in positions 4 and 5, and corresponding to the formula:

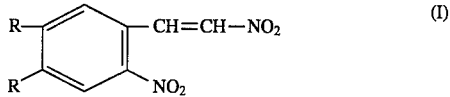

in which R denotes an acetoxy, benzyloxy or hydroxy group.

5,6-Dihydroxyindole is prepared from these compounds by means of processes comprising one or two stages.

The single-stage processes employ a cyclizing reduction with hydrogen in the presence of a catalyst such as palladium on charcoal in the case where R denotes a hydroxy group.

The known two-stage processes are essentially the following:

In a first stage, 5,6-diacetoxyindole and 5,6-dibenzyloxyindole are prepared by means of a cyclizing reduction. In the case of 5,6-dibenzyloxyindole the cyclizing reduction is carried out using iron in the presence of acetic acid. In a second stage, 5,6-dihydroxyindole is obtained:

either by deacetylation of 5,6-diacetoxyindole. This operation, carried out in an alkaline medium, does not enable the expected compound to be obtained under satisfactory conditions, bearing in mind its liability to oxidation, and this despite the presence of an antioxidant such as $Na_2S_2O_4$, or by debenzylation of 5,6-dibenzyloxyindole under hydrogen pressure in the presence of a catalyst such as palladium on charcoal. J.C.S. 2223 (1948); J. of heterocyclic Compounds 2, 387 (1965).

The stage order may be reversed; it is possible, in fact, to prepare 4,5-dihydroxy-2,β-dinitrostyrene in a first stage:

either by deacetylation of 4,5-diacetoxy-2,β-dinitrostyrene or by debenzylation of 4,5-dibenzyloxy-2,β-dinitrostyrene; in this case the debenzylation is performed by means of trifluoroacetic acid. In a second stage 5,6-dihydroxyindole is obtained from 4,5-dihydroxy-2,β-dinitrostyrene as indicated above (U.S. Pat. No. 4,595,765).

However, the use of compounds of formula I as a starting material presents other problems. The preparations of these compounds are either time-consuming and difficult to carry out, where large quantities are involved, by starting from piperonal, an industrial compound which is most frequently taken into consideration, or are performed by starting with a more costly industrial compound, 4,5-dihydroxybenzaldehyde.

On this subject, there may be mentioned the processes described in J.C.S. 2223 (1948); Chem. Ber. 93, 1318 (1969); J. of heterocycl. Compounds 2,387 (1965); J.O.C. 45,2750 (1980); patent U.S. Pat. No. 4,595,765, and Synthetic Communications 15, 321–329 (1985).

The various processes of the state of the art of the preparation of 5,6-dihydroxyindole employ seven to eight stages when the compound is prepared from piperonal, or five stages when it is prepared from 4,5-dihydroxybenzaldehyde.

The applicants have found a process for the preparation for the 5,6-dihydroxyindole from a new chemical compound corresponding to the formula:

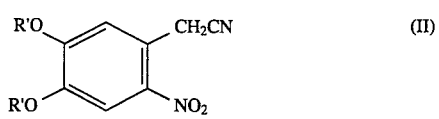

in which R' denotes a hydrogen atom or an optionally substituted benzyl group. In the case where the group R' is a benzyl group, it is unnecessary to operate in two stages, as in the case of compound I in which R=benzyloxy.

One subject of the invention, therefore, consists of the process for the preparation of 5,6-dihydroxyindole employing the compound corresponding to formula II as synthesis intermediate.

Another subject of the invention consists of the synthesis intermediates enabling 5,6-dihydroxyindole to be prepared and corresponding, in particular, to formula II.

Other subjects of the invention will become apparent from the reading of the following description and examples.

The process for the preparation of 5,6-dihydroxyindole is essentially characterized in that the compound corresponding to the formula II is subjected to the action of hydrogen under pressure, or to a hydrogen transfer operation, in a solvent medium and in the presence of a hydrogenation catalyst.

The reaction with hydrogen is performed at a pressure of between $10^5$ and $10^6$ pascals and preferably between $4\,10^5$ and $6\,10^5$ pascals.

The hydrogenation catalyst may consist, for example, of palladium or rhodium on a carrier such as charcoal.

The solvents or solvent mixtures employed do not take part in the reaction and are chosen, for example, from alcohols such as methanol, ethanol or isopropanol; esters such as ethyl or isopropyl acetate, or, yet again, from dimethylformamide, tetrahydrofurane, dioxane or diglym. It is also possible to use these solvents mixed with water.

The reaction temperature is preferably between 50° and 150° C., and in particular between 80° and 100° C.

The hydrogen transfer reaction employs a transfer agent such as cyclohexene, in the presence of a hydrogenation catalyst such as, for example, palladium or rhodium on an inert carrier, and preferably on charcoal containing 3 to 10% of metal, in the presence of a solvent or of a solvent mixture such as defined above.

By virtue of the process of the invention it is possible to prepare 5,6-dihydroxyindole in accordance with a process involving a single debenzylation and cyclization stage, by starting, more particular, from 4,5-dibenzyloxy-2-nitrophenylacetonitrile, covered by formula II.

The use, in the process according to the invention, of the debenzylating or other catalytic reduction makes it possible to obtain large quantities of product and the hydrogen transfer reaction does not require the use of any specialized hardware.

In the course of implementing the process according to the invention, the applicants observed the formation of another new intermediate, 2-amino-4,5-dihydroxyphenylacetonitrile of formula III:

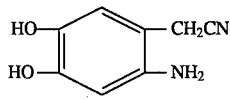

(III)

2-Amino-4,5-dihydroxyphenylacetonitrile of formula III can be isolated if, in the course of implementing the process according to the invention, the operation is carried out at a temperature between 20° and 50° C. during the catalytic hydrogenation.

The compound of the formula II, employed according to the invention, is essentially prepared using the following reaction scheme:

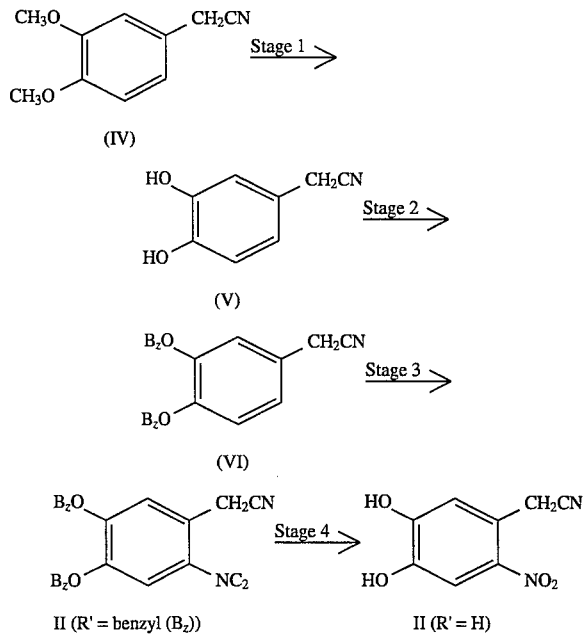

It should be noted that the intermediate compound of formula II is prepared, according to the invention, from homoveratronitrile, which is an inexpensive industrial product, and this constitutes another advantage of the invention.

Stage 1

4,5-Dihydroxyphenylacetonitrile of formula V may be prepared by demethylation of homoveratronitrile by means of pyridine hydrochloride. The yield of this reaction is particularly improved by preparing the pyridine hydrochloride in situ and by regenerating it as the reaction progresses by adding gaseous hydrogen chloride to the reaction mixture which initially consists of a mixture of homoveratronitrile and of pyridine in proportions of approximately 2 moles of pyridine per 1 mole of homoveratronitrile. This procedure makes it possible, in particular, to avoid handling pyridine hydrochloride (hygroscopic and costly) and permits a saving in the number of moles of pyridine hydrochloride per mole of homoveratronitrile. Extraction of the compound V using an organic solvent requires, at equal yields, a smaller quantity of extraction solvent.

Stages 2 and 3:

4,5-Dihydroxyphenylacetonitrile of formula V is reacted with a benzyl halide in the presence of a solvent such as, for example, dimethylformamide and an alkaline agent such as potassium carbonate, to produce 4,5-dibenzyloxyphenylacetonitrile according to formula VI. This compound is then nitrated, either with concentrated nitric acid in acetic acid, or with dilute nitric acid, to produce, 4,5-dibenzyloxy-2-nitrophenylacetonitrile of formula II (R'=benzyl).

Stage 4:

4,5-Dihydroxy-2-nitrophenylacetonitrile may be prepared by debenzylation of 4,5-dibenzyloxy-2-nitrophenylacetonitrile by hydrogen transfer, in an alcoholic or aqueous alcoholic medium. Cyclohexene is preferably used as transfer agent in the presence of a catalyst such as palladium on charcoal.

The reaction time is approximately 1 hour to 1 and ½ hours.

The process according to the invention thus makes it possible to prepare the compound II in a good yield (60 to 75%) from homoveratronitrile, using simple chemical operations.

The 5,6-dihydroxyindole prepared by following the process according to the invention is especially suitable for use in dye compositions for human keratinous fibres and more particularly for dyeing human hair.

The following examples are intended to illustrate the invention without, however, being limiting in nature.

EXAMPLES OF PREPARATION

Example 1

Preparation of 4,5-dihydroxyphenylacetonitrile (V)

Hydrogen chloride gas is bubbled through a suspension of 2 moles (354 g) of homoveratronitrile in 161 ml of pyridine, with stirring and under a nitrogen atmosphere. As soon as the temperature reaches 115° C. and becomes stable, the bubbling is discontinued; the reaction medium is heated to 170° C. for 3 hours. During this period, hydrogen chloride is bubbled through for 5 to 10 minutes at approximately half-hourly intervals. When the reaction has ended, the reaction mixture is poured into a mixture of ice and water (1.2 kg).

The expected compound is extracted with ethyl acetate. The ethyl acetate phases are combined, washed with water, and are dried over sodium sulphate. After evaporation of ethyl acetate under vacuum 292 g of the expected product are obtained. The Latter melts at 125° C.

The dry extract obtained in this manner can be used directly in the following stage.

Example 2

Preparation of 4,5-dibenzyloxyphenylacetonitrile (VI)

A mixture consisting of one mole (149 g) of 4,5-dihydroxyphenylacetonitrile prepared in stage 1, two moles of potassium carbonate (276 g) and 2.2 moles (278.5 g) of benzyl chloride in 745 ml of dimethylformamide is heated to 105°–110° C. for approximately 30 minutes. At the end of the reaction, the reaction mixture is diluted with 2.5 kg of a mixture of ice and water, and is neutralized with hydrochloric acid while being briskly stirred. The expected product, which has precipitated, is filtered off, washed with water, and is again mixed into a paste with ethanol and then with isopropyl ether.

After drying, 270 g of the expected product are obtained. This melts at 58° C.

The product obtained in this manner can be used directly in the following stage.

Analysis of a specimen recrystallized from isopropyl ether gives the following results:

| Analysis | Calculated for $C_{22}H_{19}NO_2$ | Found |
|---|---|---|
| C | 80.22 | 80.26 |
| H | 5.81 | 5.81 |
| N | 4.25 | 4.20 |
| O | 9.72 | 9.80 |

Example 3

Preparation of 2-nitro-4,5-dibenzyloxyphenylacetonitrile (compound II with R'=benzyl)

A/ by nitration in acetic acid

A solution of 0.22 mole (72.4 g) of 4,5-dibenzyloxyphenylacetonitrile in 300 ml of acetic acid is prepared.

22 ml of nitric acid (d=1.52) are added dropwise. The temperature rises to 31° C. After the heat evolution has ceased, stirring is continued for another 15 minutes. After the reaction mixture has cooled the expected product precipitates out. After filtering, washing with acetic acid and with isopropyl ether, followed by drying, 65.8 g of the expected product, which melts at 124° C., are obtained.

B/by nitration using dilute nitric acid 0.05 mole (16.45 g) of 4,5-dibenzyloxyphenylacetonitrile are added portionwise, with stirring, to 40 ml of nitric acid (d=1.40) and 40 ml of water, at a temperature of 63° C.–65° C. The product precipitates out as the addition procedes. After 10 minutes of additional stirring at 60° C., the reaction mixture is cooled. The precipitate is filtered off, washed with water and is then dried under vacuum in the presence of phosphorus pentoxide. 18.3 g of expected product, which melts at 124° C., are obtained.

The compound may be advantageously recrystallized from acetic acid.

Analysis of a specimen recrystallized from ethanol gives the following results:

| Analysis | Calculated for $C_{22}H_{18}N_2O_4$ | Found |
|---|---|---|
| C | 70.58 | 70.50 |
| H | 4.85 | 4.82 |
| N | 7.48 | 7.35 |
| O | 17.09 | 17.05 |

Example 4

Preparation of 2-nitro-4,5-dihydroxyphenylacetonitrile 0.75 g of palladium at a concentration of 10% on charcoal, to which 3 g of charcoal have been added, followed by 0.02 mole (7.5 g) of 2-nitro-4,5-dibenzyloxyphenylacetonitrile, are added with stirring to 30 ml of 96° C. ethanol containing 15 ml of cyclohexene; the reaction mixture is heated under reflux for 1 hour.

The catalyst is removed by filtration. After evaporation of the filtrate down to ¼, followed by dilution with water, the expected product precipitates out. After filtering, washing with water and drying, 3 g of the expected product is obtained; it melts at 186° C.

After recrystallization from a mixture of ethanol and water, followed by water, the elemental analysis gives the following results:

| Analysis | Calculated for $C_8H_6N_2O_4$ | Found |
|---|---|---|
| C | 49.48 | 49.33 |
| H | 3.09 | 3.11 |
| N | 14.43 | 14.42 |
| O | 32.99 | 32.80 |

Example 5

Preparation of 5,6-dihydroxyindole

A/ by hydrogen transfer 0.2 mole (74.8 g) of 2-nitro-4,5-dibenzyloxyphenyl-acetonitrile prepared in example 4 and 44.6 g of palladium at a concentration of 10% on charcoal are added with stirring to 300 ml of isopropanol containing 200 ml of cyclohexene and 30 ml of water; the reaction mixture is heated under reflux for 4 hours.

The catalyst is removed by filtration. The filtrate is evaporated to dryness; the dry extract obtained in this manner is dissolved in 500 ml of hot isopropyl ether to which charcoal has been added. The liquid is filtered hot; the filtrate is evaporated to dryness; the dry extract obtained in this manner (24 g) consists of the expected product. It melts at 142° C.

B/ by catalytic reduction

The reaction mixture is prepared in an autoclave by adding 0.04 mole (15 g) of 2-nitro-4,5-dibenzyloxyphenylacetonitrile, 1.5 g of palladium at a concentration of 10% on charcoal and 1.5 g of charcoal to 120 ml of ethanol containing 3 ml of water. These are heated to 80° C. for 2 hours, with stirring, under a hydrogen pressure of $4.10^5$ Pa. After cooling, the reaction mixture, which is treated in the same manner as previously, produces 5,6-dihydroxyindole in an equivalent yield.

Example 6

Preparation of 2-amino-4,5-dihydroxyphenylacetonitrile

The method used is the same as in the course of the preparation of 5,6-dihydroxyindole (example 58), the reaction temperature being 35°–40° C. The reaction is stopped when no further hydrogen consumption is observed. After removal of the catalyst by hot filtration, the filtrate is evaporated to dryness. It is taken up again with boiling ethyl acetate; an insoluble material is removed by hot filtration. The filtrate obtained in this manner is diluted with approximately double its volume of petroleum ether. The expected product precipitates out. After being filtered off and then washed with hot alcohol, it decomposes at 200° C.

Mass spectrum m/Z=164 (M$^+$)

$^1$H NMR: solvent: DMSO-d$_6$; reference: TMS Chemical shifts ($C_n$) 3.61 ppm 2H (singlet) 6.20 ppm 1H (singlet) 6.55 ppm 1H (singlet) unresolved bands at about 7 ppm NH$_2$, OH $^{13}$C NMR: solvent: DMSO-d$_6$; reference: TMS Chemical shifts (ppm) 18.13 ppm ($C_7$), 103.98 ppm ($C_5$), 104.74 ($C_1$); 116.32 ppm ($C_2$); 119.24 ppm ($C_8$); 136.52 ppm ($C_3$); 138.70 ppm ($C_6$); 145.57 ppm ($C_4$).

corresponding to the formula:

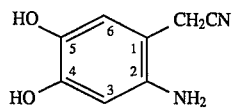

We claim:

1. A process for preparing a compound of the formula

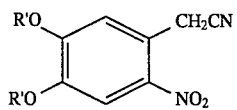

wherein R' represents benzyl, said process comprising reacting 4,5-dihydroxyphenylacetonitrile having the formula

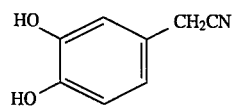

with benzyl halide in the presence of a solvent and in an alkaline medium so as to obtain 4,5-dibenzyloxyphenylacetonitrile of the formula

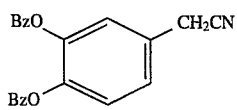

and subjecting said 4,5-dibenzyloxyphenylacetonitrile to a nitration reaction so as to prepare said compound of formula II, above.

2. The process of claim 1 wherein said compound of formula II is debenzylated in a hydrogen transfer reaction so as to produce a compound having the formula

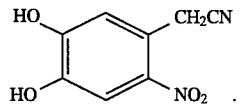

3. The process of claim 1 wherein said 4,5-dihydroxyphenylacetonitrile of formula (IV) is prepared by demethylating homoveratronitrile having the formula

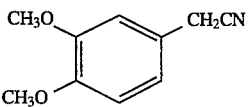

with pyridine hydrochloride prepared in situ and regenerated by the addition of hydrogen chloride.

* * * * *